(12) United States Patent
Palmer et al.

(10) Patent No.: US 10,542,926 B2
(45) Date of Patent: Jan. 28, 2020

(54) HIGH-THROUGHPUT OPERANT SENSORY DISCRIMINATION APPARATUS AND METHOD

(71) Applicant: OPERTECH BIO, INC., Philadelphia, PA (US)

(72) Inventors: R. Kyle Palmer, Cranbury, NJ (US); F. Raymond Salemme, Yardley, PA (US)

(73) Assignee: OPERTECH BIO, INC., Philadelphia, PA (US)

(*) Notice: Subject to any disclaimer, the term of this patent is extended or adjusted under 35 U.S.C. 154(b) by 0 days.

(21) Appl. No.: 16/105,601

(22) Filed: Aug. 20, 2018

(65) Prior Publication Data
US 2019/0038207 A1 Feb. 7, 2019

Related U.S. Application Data (60) Continuation of application No. 14/473,644, filed on Aug. 29, 2014, now Pat. No. 10,052,058, which is a division of application No. 11/275,059, filed on Dec. 6, 2005, now Pat. No. 8,820,265.

(51) Int. Cl.
| | |
|---|---|
| *A61B 5/00* | (2006.01) |
| *A01K 15/02* | (2006.01) |
| *A01K 1/03* | (2006.01) |
| *A01K 29/00* | (2006.01) |
| *A61D 3/00* | (2006.01) |

(52) U.S. Cl.
CPC ............ *A61B 5/4011* (2013.01); *A01K 1/031* (2013.01); *A01K 15/02* (2013.01); *A01K 29/00* (2013.01); *A61D 3/00* (2013.01); *A61B 5/4017* (2013.01)

(58) Field of Classification Search
CPC ....... A61B 5/4011; A61B 5/4017; A61D 3/00; A01K 1/031; A01K 15/02; A01K 29/00
See application file for complete search history.

(56) References Cited

U.S. PATENT DOCUMENTS

| | | | |
|---|---|---|---|
| 3,830,201 A * | 8/1974 | Coulbourn | A01K 1/031 |
| | | | 119/417 |
| 4,834,801 A | 5/1989 | Kalla et al. | |
| 5,767,385 A * | 6/1998 | Bundy | G01N 1/26 |
| | | | 73/23.34 |
| 6,234,111 B1 | 5/2001 | Ulman et al. | |
| 6,425,350 B2 | 7/2002 | Bulanda | |
| (Continued) | | | |

FOREIGN PATENT DOCUMENTS

EP 1061796 12/2000

OTHER PUBLICATIONS

Bodyak, Slotnich, "Performance of Mice in an Automated Olfactometer: Odor Detection, Discrimination and Odor Memory", 1999, Oxford University Press, Department of Psychology, American University, pp. 637-645: http://chemse.oxfordjournals.org/content/24/6/637.full.pdf.

(Continued)

*Primary Examiner* — Valentina Xavier
(74) *Attorney, Agent, or Firm* — Casimir Jones S.C.; Tyler Sisk (57) ABSTRACT

Described herein are various apparatus and systems useful in sensory discrimination. Through the use of a multi-well sample plate, the high-throughput analysis apparatus and method allow for rapid sensory discrimination of a large number of samples.

5 Claims, 6 Drawing Sheets

(56) References Cited

U.S. PATENT DOCUMENTS

| | | | |
|---|---|---|---|
| 6,426,050 | B1 | 7/2002 | Pham et al. |
| 6,899,542 | B2* | 5/2005 | Kurokawa ............. G09B 23/36 |
| | | | 119/421 |
| 6,918,309 | B2 | 7/2005 | Brock et al. |
| 7,086,350 | B2 | 8/2006 | Tecott et al. |
| 7,269,516 | B2 | 9/2007 | Brunner et al. |
| 10,052,058 | B2 | 8/2018 | Palmer et al. |
| 2001/0047771 | A1 | 12/2001 | Bulanda |
| 2003/0028327 | A1 | 2/2003 | Brunner et al. |
| 2005/0066910 | A1 | 5/2005 | Tecott et al. |
| 2006/0063202 | A1* | 3/2006 | Pieribone ........... G01N 33/5088 |
| | | | 435/7.1 |
| 2009/0077908 | A1* | 3/2009 | Brasfield ............ G01N 33/0001 |
| | | | 52/198 |
| 2015/0264892 | A1* | 9/2015 | Nir ......................... A01K 15/02 |
| | | | 119/795 |
| 2017/0006824 | A1* | 1/2017 | Baron .................... A01K 1/031 |

OTHER PUBLICATIONS

Knosys, "Knosys Olfactometers," available at http://www/knosysknosys.com/olfacto.html, 2 pages (accessed on Sep. 23, 2005).

* cited by examiner

HIGH-THROUGHPUT OPERANT SENSORY DISCRIMINATION APPARATUS AND METHOD

BACKGROUND OF THE INVENTION

Field of the Invention

The present disclosure relates to apparatus and methods for use in animal sensory discrimination.

Background of the Invention

Current designs of operant chambers used in animal sensory tests are often based on fluid delivery systems that utilize a limited number of reservoirs connected through tubing to a manifold that is in turn connected to a spout. Sample flow is often controlled by gravity. Clogging of the tubing often complicates sample delivery. Although this type of apparatus does provide some insight into what the animal senses, such designs limit the number of solutions that can be sampled by an animal, as well as the rate at which they can be tested.

An alternative approach to taste measurement that is higher throughput uses an apparatus usually referred to as a "lickometer," which records the number of "licks" or tastes that an animal takes of a particular sample. This method, however, only provides an indication of whether a solution is avoided or preferred, and therefore does not provide a direct indication of whether the sample is similar to or different from what the animal has been trained to detect, e.g., salty, sweet, spicy, bitter, etc.

What is needed is a sensory discrimination apparatus that allows multiple samples to be rapidly tested, and also allows a direct measure of the sensory perception of the animal.

SUMMARY OF THE INVENTION

This disclosure provides apparatus and methods for use in animal sensory discrimination. A high-throughput, multiple sample apparatus is provided that allows for rapid sampling of any number of test samples by a subject, all within a self-contained, low contamination environment. Exemplary embodiments allow for sampling of a plurality of separate sensory samples that require very small amounts of sample.

Further embodiments, features, and advantages, as well as the structure and operation of the various embodiments are described in detail below with reference to accompanying drawings.

BRIEF DESCRIPTION OF THE FIGURES

The disclosure is described with reference to the accompanying drawings. In the drawings, like reference numbers indicate identical or functionally similar elements.

DETAILED DESCRIPTION OF THE INVENTION

It should be appreciated that the particular implementations shown and described herein are examples and are not intended to otherwise limit the scope of the disclosure in any way.

An apparatus for use in animal sensory discrimination is provided, comprising: a support platform, means for supporting one or more samples, means for signaling an animal to sample the contents of the one or more samples, and means for obtaining the animal's response to the sampled one or more samples.

As used herein, the term animal refers to animals of any species, including, but not limited to, mice, rats, rabbits, hamsters, guinea pigs and non-human primates (e.g., baboons, monkeys, and chimpanzees).

Figure 1:
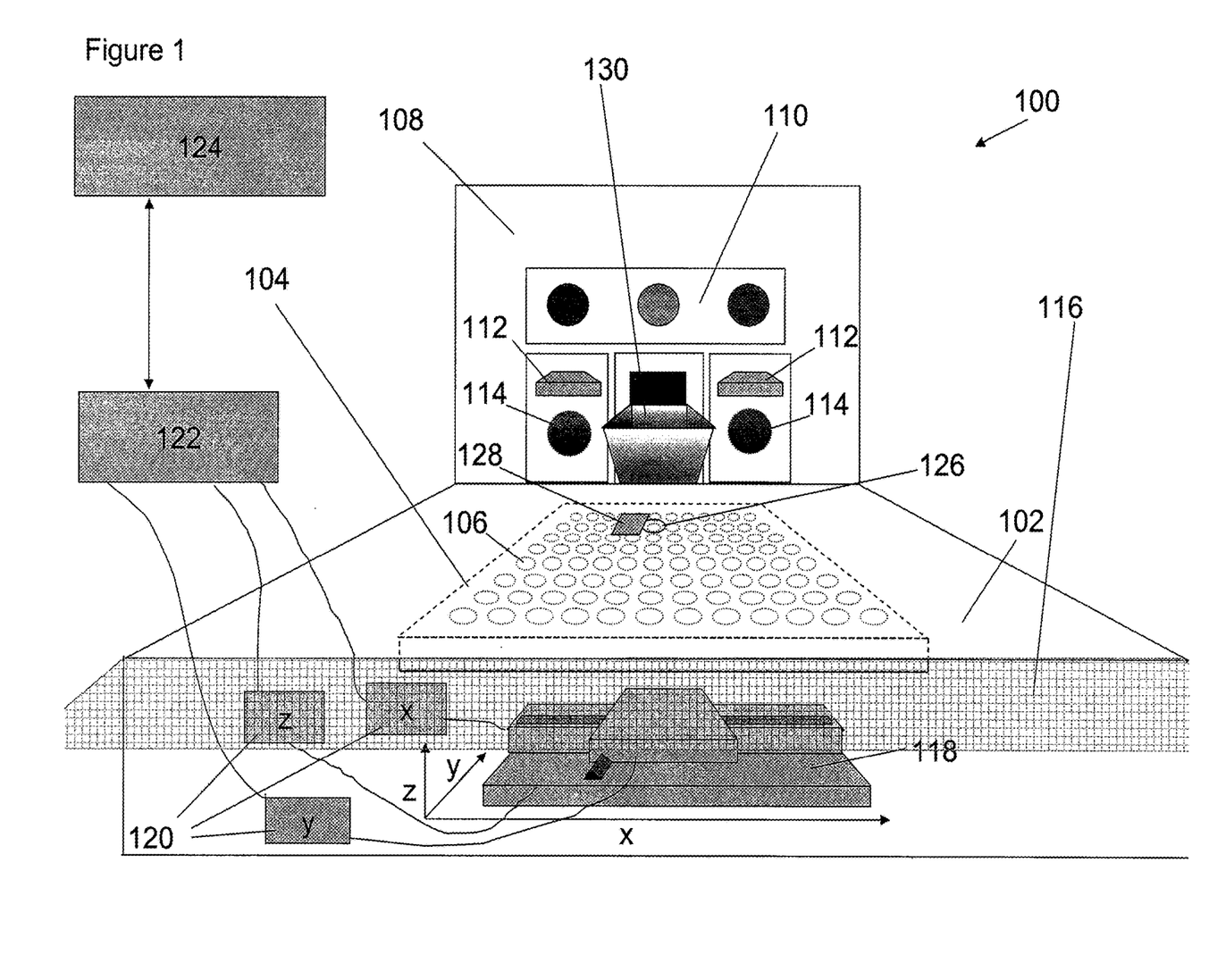
FIG. 1 shows an exemplary sensory discrimination apparatus.

FIG. 1 shows an exemplary apparatus 100 for use in animal sensory discrimination. As shown in FIG. 1, apparatus 100 comprises a support platform 102. Suitably, support platform 102 will be a stainless steel or other material plate or floor, but can be any similar support platform on which an animal can be positioned, e.g. a table top, lab bench, cart or the like. In addition, the animal can be supported by other means, for example a sling, net, or similar device that supports the animal while it is participating in sensory discrimination analysis. Additional means for supporting the animal during analysis can be readily determined by the skilled artisan and used in the apparatus and methods described herein. Support platform 102 suitably comprises an area large enough such that an animal can position itself to gain access to a sample support means 104. A grid floor 116, suitably screen mesh or bars of an animal cage, lies adjacent, and in same plane as support platform 102 (suitably an extension of support platform 102). Grid floor 116 is designed to allow animal waste to pass through, and may constitute part of the animal's temporary or permanent housing.

As shown in FIG. 1, apparatus 100 also comprises means for supporting the one or more samples, such as a sample plate 104 having a plurality of sample wells 106 formed therein. As used herein, the term plurality is used to indicate more than 1 of an item. For example, a plurality of sample wells indicates 2, 3, 4, 5, 10, 20, 30, 40, 50, 100, 200, 300, etc. sample wells. Means for supporting one or more samples also includes additional means readily determined by the skilled artisan. In suitable embodiments, sample support means comprises a sample plate comprising about 4 to about 100 sample wells, for example, about 4, 6, 12, 24, 48 or 96 wells. Larger size sample plates can also be used, for example sample plates comprising 192 wells, 384 wells, etc.

As shown in FIG. 1, apparatus 100 also comprises means for signaling an animal to sample the contents of the one or more samples. Signaling means suitably comprise an operant panel 108, having one or more signal lights 110. Operant panel 108 is a modular unit that comprises means for signaling the animal as well as means for obtaining the animal's response to the sample(s) and means for rewarding the animal (discussed below). Any combination of signaling means and rewarding means (as well as additional functionalities) can be interchanged in operant panel 108. Means for signaling the animal, in addition to signal lights 110, may include signal buzzers, alarms, bells or other noise making devices, additional visual signals, such as moving panels or flags and the like. Means for signaling the animal also include additional means readily determined by the skilled artisan.

Apparatus 100 also comprises means for obtaining the animal's response to the sampled one or more samples. Exemplary means for obtaining the animals' response include one or more levers 112 and/or one or more nose poke wells 114, as part of operant panel 108. Means for obtaining the animal's response to the sampled one or more samples can be used in various combinations. For example, a lever can be used for obtaining a response to one type of sample and a nose poke well can be used for obtaining a response to another type of sample. While FIG. 1 shows the use of two levers 112 and two nose poke wells 114, any combination or number of such means for obtaining the animal's response can be used. Upon contact by the animal (e.g., being pressed by the animal's nose or paw), levers 112 generate a signal that indicates that the animal has recorded its response to a sample. Nose poke wells 114 often comprise a light beam or similar device, such that when the nose (or paw) of the animal breaks the plane of the light beam, a signal is generated that indicates that the animal has recorded its response to a sample. Additional means for obtaining the animal's response to the samples include licking spouts, chain pulls (e.g., for use with primates) and the like. Means for obtaining the animal's response to the samples include additional means readily determined by the skilled artisan.

Animals can be trained to sample and recognize any number of different kinds of sensory stimuli, and then respond accordingly. For example, one lever (the left lever 112 for example) is contacted when the animal samples a sample that it has been trained to recognize. In such a scenario, an additional lever (the right lever 112 for example) is contacted when the animal samples a sample that it has not been trained to recognize. For example, if the animal has been trained to recognize bitter-tasting samples, and it samples something that it determines is not bitter (e.g., sweet, spicy, salty, or control—i.e. no real discernable flavor), it would contact the right lever. However, upon sampling something bitter, it would contact the left lever indicating that the sample has a taste similar or identical to what it has been trained to recognize. Such a scenario can be carried out using the nose poke wells 114, or nose poke wells in combination with levers 112, in a similar manner. The animal can also be trained to recognize several different types of samples, and thus three or more levers (or nose poke wells) can be used during such an analysis (e.g. one lever for sweet, one lever for salty, one lever for not-trained to recognize).

As shown in FIG. 1, apparatus 100 can also further comprise means for moving sample support means 104 and support platform 102 relative to each other. Moving means suitably is able to move sample support means, e.g. sample plate 104, and support platform 102, relative to each other in at least two orthogonal directions. Moving means, as shown in FIG. 1, can be, for example, a motion table 118. As shown in FIG. 1, motion table 118 can move sample plate 104 in both the x and y directions, i.e. in the plane of sample support 104. In addition, motion table 118 can also be equipped to move sample plate 104 in the z direction, i.e. normal to the plane of support platform 102. Motion table 118 can be a single direction motion table (i.e., x, y, or z), an x-y motion table or an x-y-z motion table, or any combination thereof. As shown in FIG. 1, motion table 118 is connected to drivers 120 (x, y and/or z directions), an interface 122 and a computer 124 that control the motion of motion table 118, specifically controlling the timing, direction and distance that sample support means 104, and/or support platform 102, are moved. Moving means can also comprise a mechanism by which support platform 102 is moved relative to sample plate 104, while keeping sample plate 104 stationary, or both support platform 102 and sample plate 104 can be moved relative to each other at the same time. Means for moving sample support means and support platform relative to each other include additional means readily determined by the skilled artisan.

Apparatus 100, as shown in FIG. 1, can also further comprise means for concealing the one or more samples. Concealing means can comprise one or more movable partitions. As used herein, the term movable partitions includes partitions such as, but not limited to, sliding doors, panels, curtains, levers, barriers, gates, hatches, walls, dividers and the like. Means for concealing the one or more samples include additional means readily determined by the skilled artisan.

For example, sample support means can be accessible to the animal at all times (e.g., positioned on the support platform with the animal), but the individual samples (e.g., wells 106) on the sample support means (e.g., support plate 104) can either be collectively or individually concealed from the animal. In such embodiments, each individual sample can be concealed from the animal, for example by placing a door or panel over each separate sample, or all of the samples can be collectively concealed from the animal, for example by using a door, panel or curtain to conceal the sample. When the partition is removed, the animal is then able to sample the individual sample, or collectively all of the samples, or any combination thereof.

In exemplary apparatus 100 shown in FIG. 1, sample support means, i.e. sample plate 104, is oriented below support platform 102. It should be understood that the spatial descriptions (e.g., "above", "below", "up", "down", "top", "bottom", etc.) made herein are for purposes of illustration only, and that the apparatus described herein be spatially arranged in any orientation or manner. As shown in FIG. 1, support platform 102 can comprise one or more apertures 126 that allow access to sample support means (e.g., sample plate 104) situated below support platform 102. Aperture 126 is shown as a circular hole in support platform 102, but it should be understood that aperture 126 can be of any size or orientation that allows access to the sample support means. In addition, multiple apertures 126 can be made in support platform 102, such that multiple, or even every, individual samples on the sample support means (e.g., wells 106 formed on sample plate 104) are accessible to the animal.

In addition to one or more apertures 126, support platform 102 can also comprise means for concealing the sample support means, such as one or more partitions 128 covering one or more apertures 126. For example, if the sample support means (e.g., sample plate 104) is oriented below support platform 102, such that sample plate 104 can be accessed by an animal on support platform 102 through one or more apertures 126, one or more partitions 128 can be used to conceal sample plate 104 from the animal by covering over apertures 126 until such time that the operator wishes to reveal the sample(s) to the animal. As discussed throughout, partition 128 can comprise a sliding door or panel or other suitable concealing device that can then be moved to reveal a well 106 on sample plate 104 below the support platform 102.

As shown in FIG. 1, apparatus 100 can also further comprise means for rewarding the animal, for example, food hopper 130. Other means for rewarding the animal, for example, a water dispenser, salt lick, toy or other reward mechanism can also be used. In addition, means for rewarding the animal can include some form of physical or other rewarding stimulation (e.g., petting, grooming, etc.) Means for rewarding the animal include additional means readily determined by the skilled artisan.

Figure 2:
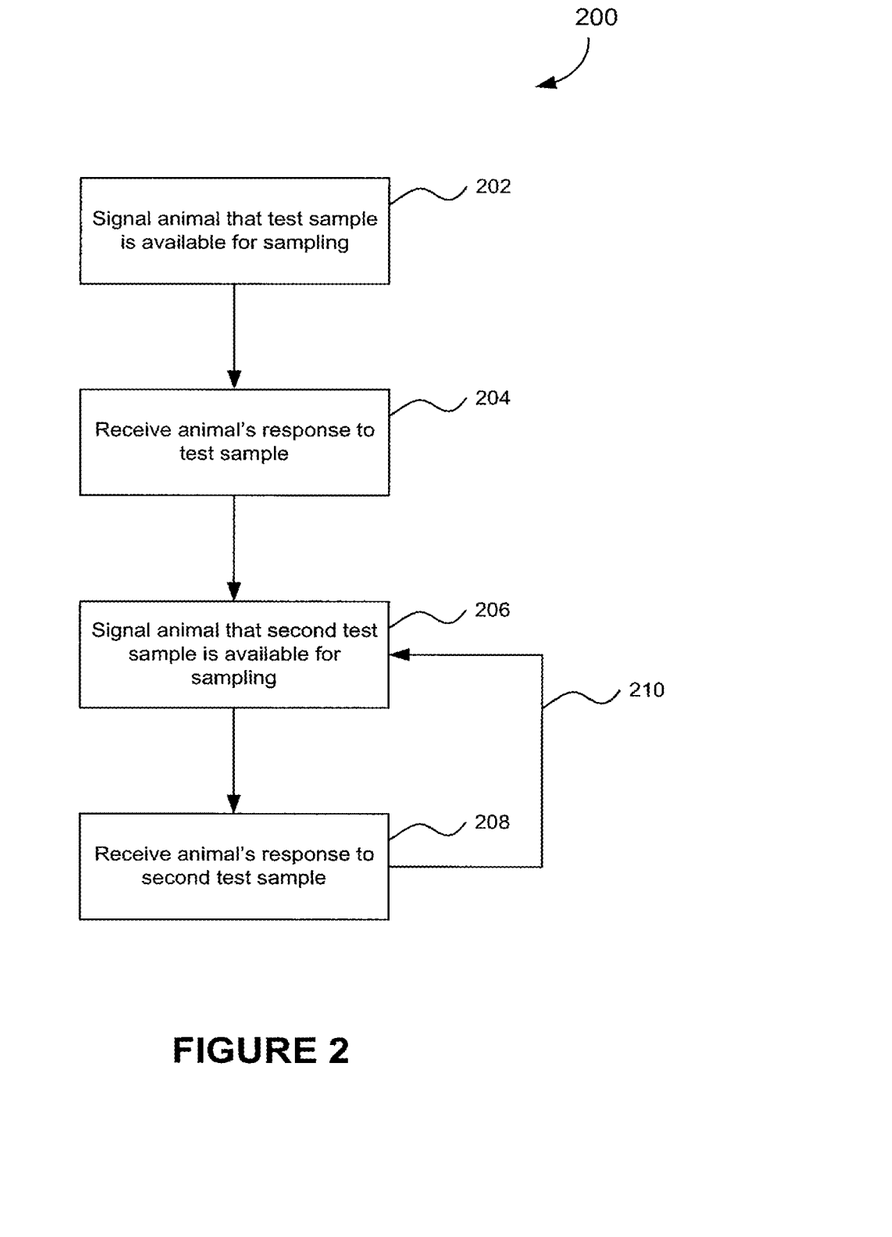
FIG. 2 shows a flowchart of a method for carrying out sensory discrimination.

FIG. 2 shows a flowchart 200 describing a method of obtaining an animal's response to one or more test samples for use with an apparatus comprising: a support platform, means for supporting one or more samples, means for signaling an animal to sample the contents of the one or more samples, and means for obtaining the animal's response to the sampled one or more samples.

In step 202, an animal is signaled that a test sample is available for sampling. In step 204, the animal's response to the test sample is received. The animal can be signaled that a sample is available for sampling using any suitable means described herein or known in the art. For example, a signal light, bell, whistle, alarm or other signaling means can be used to signal the animal that a test sample on the sample support means is available for sampling.

After the animal has sampled the contents of the sample, the animal's response to the sample is received through the use of means for obtaining the animal's response. (The terms "received" and "obtained" are used interchangeably herein as they pertain to the animal's response). For example, the animal may contact a lever, or trigger a nose-poke well, to indicate that it has sampled the contents of the sample and determined that it is something it has been trained to recognize, or, alternatively, that it is not something it has been trained to recognize.

Following obtaining the animal's response to the first sample, at step 206, the animal is signaled that a second test sample is available for sampling. In step 208, the animal's response to the second test sample is then received. As shown in step 210, steps 206 and 208 can be repeated until all of the samples have been sampled by the animal (i.e. the animal is signaled that a third, fourth, etc., sample are available for sampling and then the animal's response to each additional sample is received).

Figure 3:
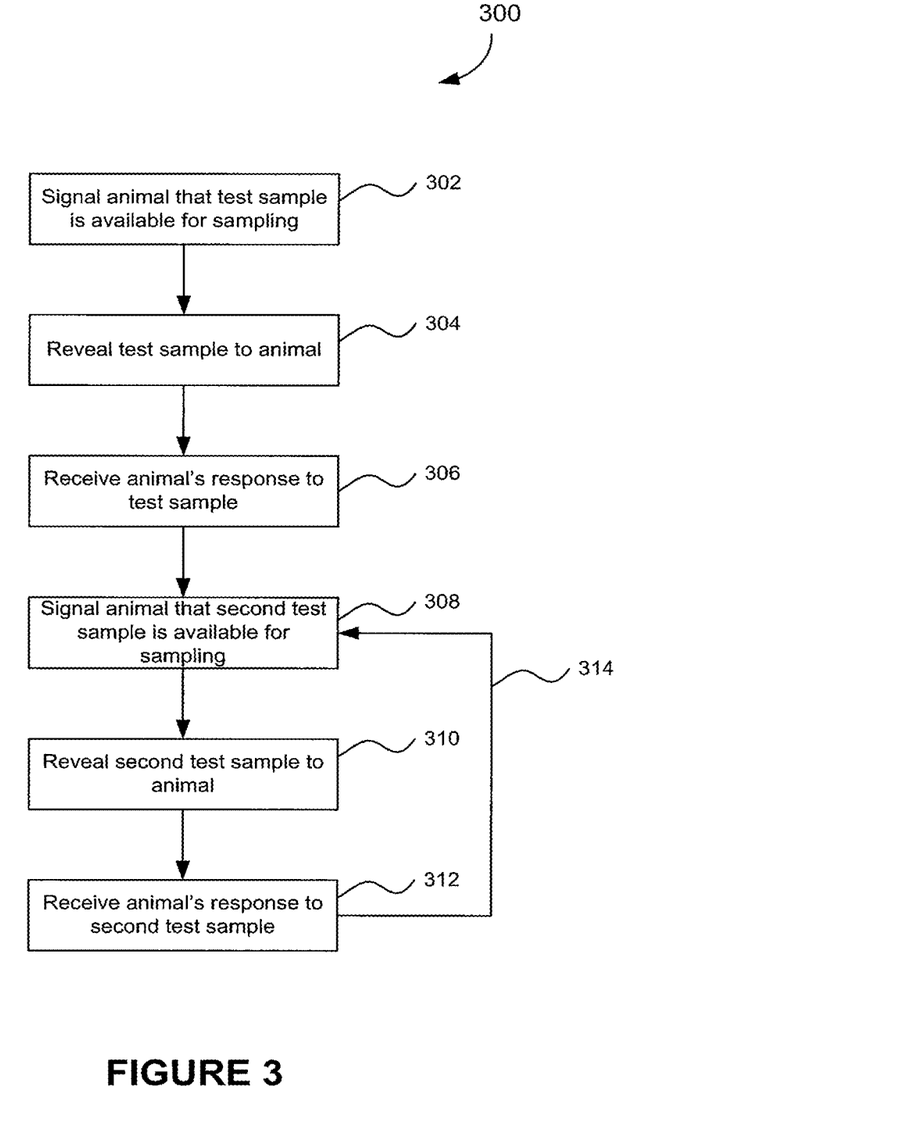
FIG. 3 shows a flowchart of another method for carrying out sensory discrimination.

FIG. 3 shows a flowchart 300 describing another method of obtaining an animal's response to one or more test samples for use with an apparatus comprising: a support platform, means for supporting one or more samples, means for concealing the one or more samples, means for signaling an animal to sample the contents of the one or more samples, and means for obtaining the animal's response to the sampled one or more samples.

In step 302, an animal is signaled that a test sample is available for sampling. The animal can be signaled that a sample is available for sampling using any suitable means disclosed herein or known in the art. In step 304, a test sample is revealed to the animal. Any means suitable for concealing a test sample, and then revealing the test sample to the animal, can be used. For example, a movable door, panel or other partition can be used to conceal the sample from the animal, and then moved to reveal the sample to the animal. Additional means for revealing the sample to the animal include those described herein or known in the art. The steps of signaling the animal that a sample is available for sampling 302 and revealing the sample to the animal 304 can be performed in any order. In step 306, the animal's response to the test sample is received. Suitable means for receiving/obtaining the animal's response to the test sample include those described herein as well as additional means known to those skilled in the art.

At step 308, the animal is signaled that a second test sample is available for sampling. In step 310, this second test sample is revealed to the animal, and in step 312, the animal's response to the $2^{nd}$ sample is received/obtained. Suitable means for performing these various steps include those described herein as well as additional means known to those skilled in the art. In step 314, steps 308 through 312 can then be repeated until all of the samples have been sampled by the animal (i.e. the animal is signaled that a third, fourth, etc., sample are available for sampling, the additional sample(s) are revealed to the animal, and then the animal's response to each additional sample is received).

Figure 4:
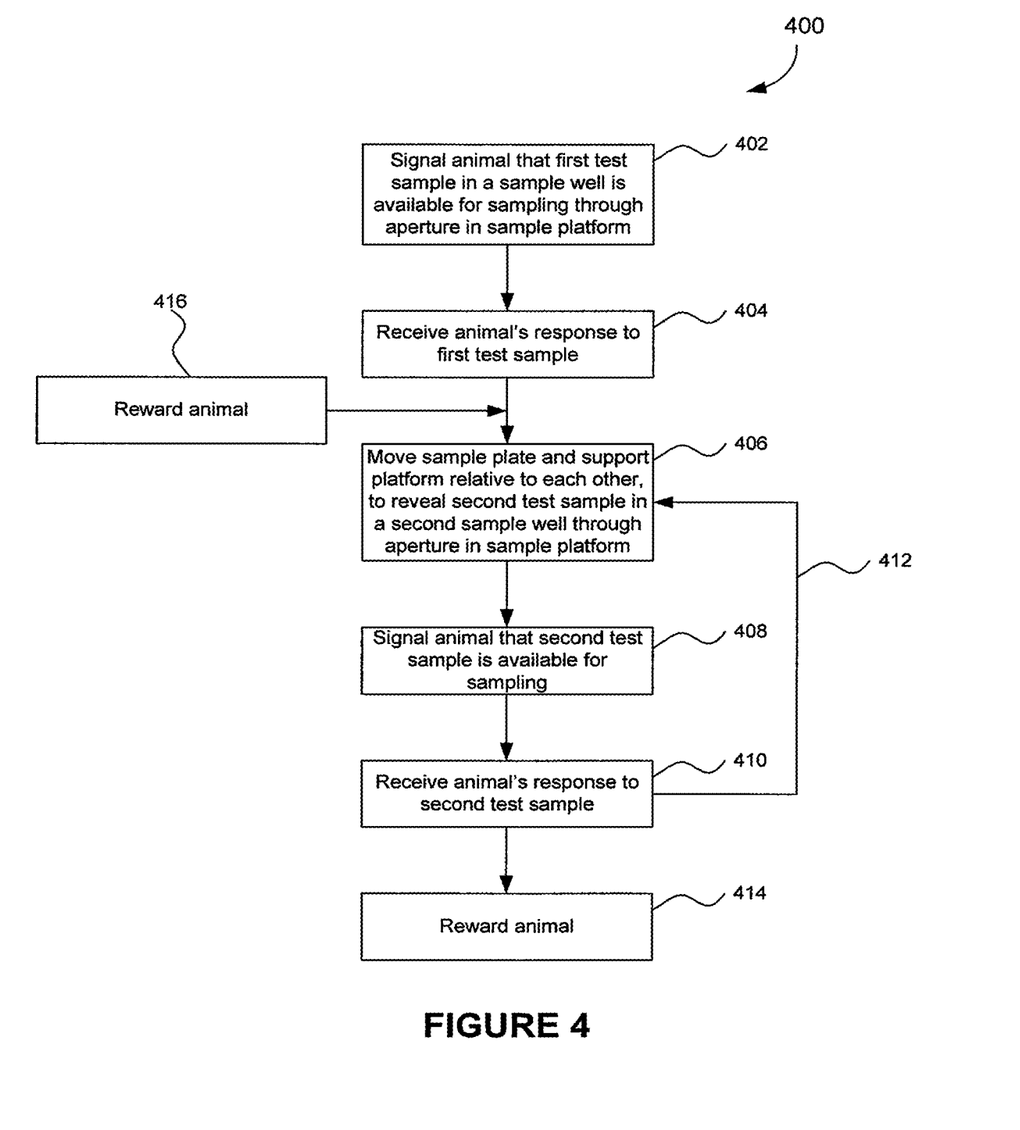
FIG. 4 shows a flowchart of a further method for carrying out sensory discrimination.

FIG. 4 shows a flowchart 400 describing a further method of obtaining an animal's response to one or more test samples for use with an apparatus comprising: a support platform comprising one or more apertures, a sample plate having a plurality of sample wells formed therein oriented below the support platform, means for moving the sample plate and the support platform relative to each other, means for signaling an animal to sample the contents of the one or more sample wells, and means for obtaining the animal's response to the sampled contents.

In step 402, an animal is signaled that a first test sample in a sample well is available for sampling through an aperture in the sample platform. For example, as shown in FIG. 1, a first sample well 106 is positioned below aperture 126 and the animal is signaled that the first sample is available for sampling. The animal can be signaled that a sample is available for sampling using any suitable means described herein or known in the art. For example, signal lights 110, can be used to signal the animal. In step 404, the animal's response to the first sample is received/obtained. Suitable means for obtaining the animal's response to the first test sample include those described herein and additional means known to those skilled in the art. For example, the animal's response can be obtained by the animal contacting one or more levers 112 and/or activating one or more nose-poke wells 114.

In step 406, the sample plate and the support platform are moved relative to each other to reveal a second test sample in a second sample well through the aperture in the sample platform. For example, as shown in FIG. 1, after the first sample in a sample well 106 has been sampled and the response received, the sample plate 104 is moved (e.g., through the use of motion table 118) so that a second sample well 106 containing a second sample is positioned beneath aperture 126 in support platform 102. In other embodiments, support platform 102 can be moved relative to sample plate 104, or both can be moved relative to each other. Means for moving sample plate 104 and support platform relative to each other include those described herein as well as additional such means known to those skilled in the art. In step 408, the animal is signaled that the second test sample is available for sampling (e.g., using signal lights 110). It should be understood that the steps of moving the sample plate 104 and support platform 102 relative to each other to reveal a second sample, and the step of signaling the animal to sample the second sample 408 can be performed in any order.

In step 410, the animal's response to the second test sample is received/obtained (e.g., by the animal contacting one or more levers, 112, or activating one or more nose-poke wells, 114). In step 412, steps 406 through 410 are then repeated until all of the samples have been sampled by the animal (i.e. the sample plate 104 and the support platform 102 are moved relative to each other to reveal a third, fourth, etc., sample; the animal is signaled that third, fourth, etc., samples are available for sampling; and the animal's response to each additional sample is received).

In step 414, the animal is rewarded for completing the sampling task(s). In additional embodiments, flowchart 400 can optionally comprise rewarding the animal in step 416 after it has provided a response to the first sample in step 404. Suitable means for rewarding the animal include those described herein, as well as additional means known to the skilled artisan. For example, the animal can be rewarded by being allowed to eat from food hopper 130.

Figure 5:
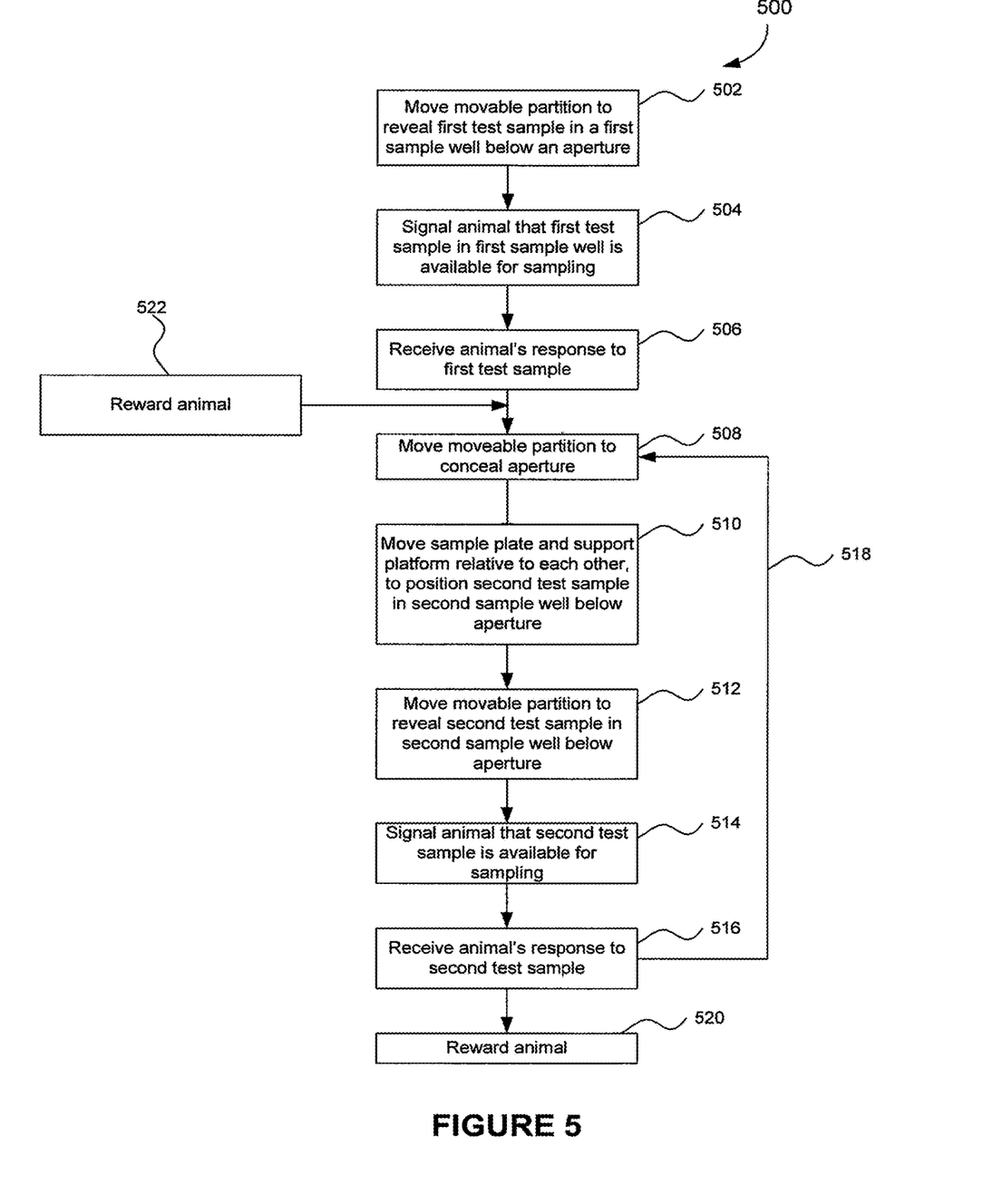
FIG. 5 shows a flowchart of a still further method for carrying out sensory discrimination.

FIG. 5 shows a flowchart 500 describing a still further method of obtaining an animal's response to one or more test samples for use with an apparatus comprising: a support platform comprising one or more apertures and one or more movable partitions concealing the apertures, a sample plate having a plurality of sample wells formed therein oriented below the support platform, means for moving the sample plate and the support platform relative to each other, means for signaling an animal to sample the contents of the one or more sample wells, means for obtaining the animal's response to the sampled one or more contents, and means for rewarding the animal.

In step 502, (with reference to FIG. 1) a movable partition 128 is moved to reveal a first test sample in a first sample well 106 below an aperture 126 in support platform 102. In step 504, the animal is signaled that the first test sample in the sample well 106 is available for sampling. Any suitable means for signaling the animal, such as those described herein or known to those skilled in the art, can be used. For example, the animal may be signaled through the use of one or more signal lights 110. It should be understood that the steps of moving the movable partition to reveal the test sample 502 and signaling the animal that the test sample is available for sampling 504 can be performed in any order. In step 506, the animal's response to the first test sample is then received/obtained. Any suitable means for obtaining the animal's response to the sample may be used, such as those described herein, as well as additional means known to those skilled in the art. For example, the animal's response can be received by the animal contacting one or more levers 112 or activating one or more nose-poke wells 114.

In step 508, the movable partition 128 is then moved so as to conceal the aperture 126 in support platform 102. In step 510, sample plate 104 and support platform 102 are moved relative to each other, thereby positioning a second test sample in a second sample well 106 below aperture 126 in support platform 102, for example by using motion table 118.

In step 512, movable partition 128 is moved to reveal the second test sample in the second sample well 106. In step 514, the animal is signaled that the second test sample in the sample well is available for sampling. It should be understood that steps 512 and 514 of respectively moving the movable partition to reveal the second test sample, and signaling the animal that the second test sample is available for sampling, can occur in any order. In step 516, the animal's response to the first test sample is then received/obtained. For example, the animal's response can be received by the animal contacting one or more levers 112 or activating one or more nose-poke wells 114. In step 518, steps 508 through 516 are repeated until all test samples have been sampled by the animal. After all test samples have been sampled by the animal (i.e., constituting a completed analysis session), the animal is rewarded in step 520, for example, by allowing the animal to eat from food hopper 130. In additional embodiments, flowchart 500 can optionally comprise rewarding the animal in step 522 after it has provided a response to the first sample in step 506. In still further embodiments, the animal can be rewarded following the completion of each and every sample, or a select number of samples, as desired, during the analysis session.

Figure 6:
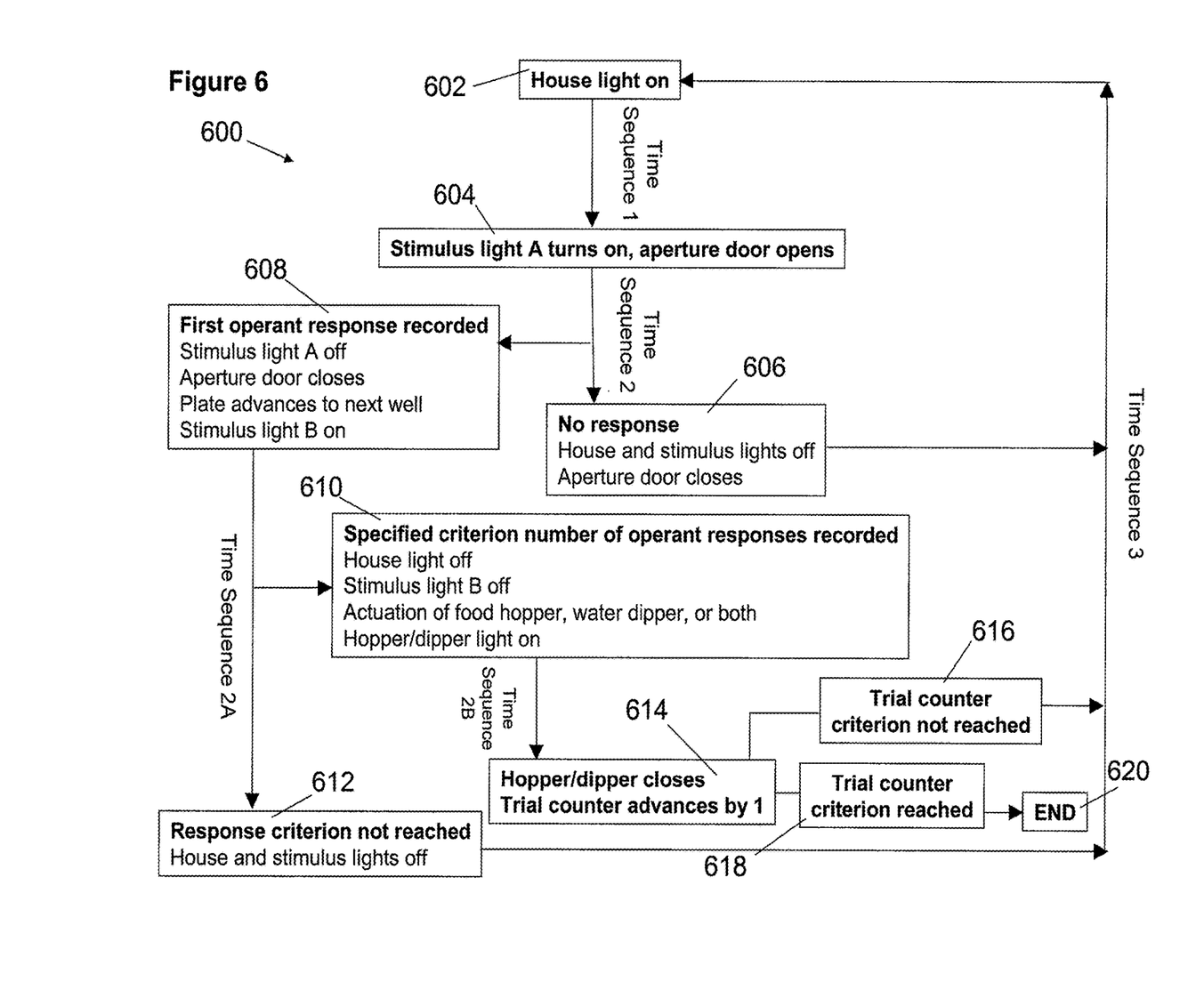
FIG. 6 shows a flowchart of an exemplary sensory discrimination session.

Flowchart 600 in FIG. 6 (with reference to FIG. 1) shows an example of a sensory discrimination session that can be produced using the apparatus and methods described herein, and the various iterations/scenarios that can occur during the session. It should be understood that the session described in flowchart 600 represents only a set of possible scenarios, and other sensory discrimination sessions/scenarios can be produced using the methods and apparatus described herein, and will be readily apparent to those skilled in the art. The various steps or "actions" noted in FIG. 6 can be coordinated through the use of suitable computer-based or other automated controls. The design of computer programs to control the apparatus and execution of the steps/actions noted in FIG. 6 (as well as additional steps/actions described herein) are easily accomplished by, and well known to those skilled in the art. In addition, the various steps/actions can also be conducted manually, e.g., by a human operator.

In step 602, a house light (e.g., general light in the animal's housing, not shown in FIG. 1) is turned on, indicating to the animal that a sensory discrimination session is about to begin. In step 604, a first signal light 110 (e.g., A) is turned on, indicating to the animal that a sample is ready to be sampled. Either before, after, or simultaneously with the illumination of signal light A, aperture 126 is opened by sliding or otherwise moving movable partition 128. In one possible scenario, as noted in step 606, the animal may not sample the sample, or if it does, may simply not respond to the sample. In such a scenario where no response is received, after a pre-set amount of time (e.g., on the order of a few minutes), the session is reset, i.e. the house and signal lights are shut off, the aperture door is closed, and the session is re-set back to step 602. As noted above, this can be accomplished manually by an operator, or it can be automated through the use of a computer-control system.

In a second possible scenario, as shown in step 608, the animal actually responds to the first sample. That is, the animal samples the sample and then "records" its response to the sample by, for example, contacting one or more levers 112 or activating one or more nose-poke wells 114, or other means for obtaining the animal's response, such as those described herein. Once the animal's response to the first sample has been obtained, the first signal light 110, A, is turned off, movable partition 128 is moved so as to close aperture 126 and support platform 102 and sample support means (e.g., sample plate 104) are moved relative to each other such that a second test sample (for example in a second sample well 106) is positioned beneath aperture 126. A second signal light 110, B, is also turned on at this time. This second signal light indicates to the animal that analysis of the first sample has been successfully completed.

In most analysis sessions, a specified criterion number of samples/responses will be required prior to rewarding the animal, or stopping the analysis session. In step 612, if it is determined that the response criteria have not been reached (i.e. not enough samples sampled/recorded by the animal, for example, only the first sample out of 5 required), the house and stimulus lights are turned off, and the analysis session is re-set back to step 602 to allow the animal to sample the second test sample (i.e. the second test sample that was moved under aperture 126 in step 608). Steps 604 and 608 are then repeated as described above, recording the animal's response to the second test sample (or the system is re-set in step 606 if the second sample is not sampled/ recorded). In step 608, a third test sample is then positioned below aperture 126. If it is determined that the specified criterion number of responses has still not been reached, step 612 will re-set the analysis session back to step 602, and the sequence will continue. This loop (time sequence 1, time sequence 2, time sequence 2A and time sequence 3 as designated in flowchart 600) will continue until the specified criterion number of responses are recorded (i.e. sampled/recorded by the animal).

In step 610, once the specified number of operant responses are recorded, (i.e. the last requisite sample is sampled and recorded in step 608) the house lights are turned off, the signal light 110, B, is turned off, and the animal is rewarded, for example through the use of food hopper 130, water dipper, and/or other means for rewarding the animal. For example, 5 test samples may be required to be sampled and recorded by the animal in order to reach the specified number of criterion responses. Any number of responses though can be used as the criterion for determining when the animal is rewarded or the analysis is complete (e.g, 1, 2, 3, 4, 5, 10, 15, 20, 30, 40, 50, etc. samples/responses).

Once the animal has been rewarded, the analysis session then enters time sequence 2B as shown in flowchart 600. In step 614, the animal reward means is closed, and a counter is advanced by 1, indicating the successful completion of one test session (i.e. sampling and recording of the requisite number of samples). In steps 616 and 618, it is determined whether or not the criteria of the complete analysis session have been reached. For example, if the analysis session is designed to test a total of 50 samples, and the specified criterion number of responses required for the animal to be rewarded (step 610) is set at 5, then 10 total test sessions are required to complete the full analysis session (i.e. 10 sets of 5 animal sampling/responses). In the case where the entire analysis session has not been completed (i.e. all 50 samples), step 616 then resets the analysis session back to step 602 (time sequence 3) and the sampling/response analysis discussed above is repeated. If it is determined that the entire analysis session has been completed, step 618 then signals that the session is to be ended, in step 620.

The apparatus and methods described herein therefore allow for an animal to sample and analyze a large number of samples in a very rapid manner. For example, if a 96 well plate is used as sample support means, 96 total samples can be analyzed by a single animal (or multiple animals if desired) in a single analysis session. For example, the specified criterion number of responses required for the animal to be rewarded can be set at 4 (or any number). Thus, the animal will be rewarded after the completion of every 4 samples sampled/recorded. The system is then reset in steps 614-616 until 24 iterations are completed (i.e. 4×24=96 total samples). The analysis system and apparatus can be used to sample any number of samples, e.g., 2, 3, 4, 5, 10, 20, 30, 40, 50, 100, 200, 300, etc., using the iterative methods and apparatus described herein.

The use of sample support means such as sample plate 104 (e.g., a 6, 12, 24, 48, 96, 192 or 384 well sample plate) allows a user to utilize very small sample sizes in various sensory discrimination analyses. For example, in the case of liquid samples, sample sizes on the order of 10's to 100's of microliters can be used (or larger volumes can be used as well). This is highly advantageous for samples that may be expensive or difficult to produce in large quantities. This volume (e.g., 10 µL) in the well of a 96 well sample plate though, is more than adequate for an animal to sample and record a sensory response. In addition to liquid samples, solid samples can also be used in the various apparatus and methods described herein.

While taste discrimination is one example of a sensory analysis that can be performed using the methods and apparatus described herein, additional sensory discrimination tests can also be performed. For example, olfactory sensory discrimination can be tested by using a sample support means that comprises large/deep wells 106, thereby allowing larger amounts of volatile samples to be used to facilitate analysis by the animal.

The apparatus and methods described herein can also be used for selective delivery of food or medicine to an animal. For example, the apparatus and methods can be used to selectively move the sample support means and support platform relative to one another and/or move the movable partition to reveal a specific type of food or medicine to an animal at a predetermined time, or predetermined amounts at various times. The apparatus and methods described herein can also be used in various other discrimination settings beyond sensory discrimination. For example, the effects of one or more pharmaceuticals, toxins, or other agents can be assessed using the various systems and methods described herein.

It will be readily apparent to one skilled in the relevant arts that other suitable modifications and adaptations to the methods and applications described herein can be made without departing from the scope of the disclosure or any embodiment thereof. The examples presented herein are for purposes of illustration, and not limitation. Alternatives (including equivalents, extensions, variations, deviations, etc., of those described herein) will be apparent to persons skilled in the relevant art(s) based on the teachings contained herein. Such alternatives fall within the scope and spirit of the disclosure.

What is claimed is:

1. An apparatus for high throughput testing of a plurality of samples comprising:
    a plate having a plurality of wells formed therein, wherein between 10 and 2000 microliters of a sample for testing is present in one or a plurality of the wells;
    a means of signalling to a subject that a sample in one of the sample wells is to be tested;
    means for the subject to record a response to the tested sample; and
    means for receiving and recording the subject's response;
    wherein the apparatus comprises a computer that:
    1) identifies a sample to be tested from the plurality of wells and makes the sample available to the subject;
    2) activates the signalling means;
    3) controls the amount of time a subject can test and record a response to the sample;
    4) receives and records the subject's response to the sample; and
    5) repeats steps 1 through 4 until a response is received and recorded for each sample of the plurality of samples, wherein steps 1 through 4 occur within an order of a few minutes.

2. The apparatus of claim 1, wherein the plate comprises between about 12 and 384 wells.

3. The apparatus of claim 1, wherein the plate comprises 12, 24, 48, or 96 wells.

4. The apparatus of claim 1, wherein between 4 and 300 unique samples are present in the plate.

5. The apparatus of claim 1, wherein the apparatus further comprises means for rewarding the subject after the subject has completed sample testing.

\* \* \* \* \*